United States Patent [19]

Lin et al.

[11] 4,219,495

[45] Aug. 26, 1980

[54] METHOXYMETHYL P-TOLUENESULFONATE

[75] Inventors: Jeng S. Lin, Clay; Paul D. Sleezer, DeWitt, both of N.Y.

[73] Assignee: Bristol-Myers Company, New York, N.Y.

[21] Appl. No.: 16,453

[22] Filed: Feb. 28, 1979

[51] Int. Cl.³ .................. C07C 143/68; C07D 499/08
[52] U.S. Cl. ........................ 260/456 P; 260/239.1; 260/239.3 A
[58] Field of Search .................................... 260/456 P

[56] References Cited

U.S. PATENT DOCUMENTS

| | | | |
|---|---|---|---|
| 3,737,447 | 6/1973 | Mazur et al. | 260/456 R |
| 3,843,639 | 10/1974 | Sapino, Jr. et al. | 424/246 |
| 3,996,236 | 12/1976 | Sleezer et al. | 260/306.7 C |
| 4,125,716 | 11/1978 | Crast, Jr. et al. | 544/28 |

FOREIGN PATENT DOCUMENTS 1488308 10/1977 United Kingdom ............. 260/306.7 C

OTHER PUBLICATIONS

Karger et al., JACS, 90, 3878 (1968).
Karger et al., JACS, 91, 5663 (1969).
Yardley et al., Synthesis, Apr. 1976, p. 244.
Fuji et al., Synthesis, Apr. 1975, p. 276.
Federal Register, 39, 1910.93h (Jan. 29, 1974).

*Primary Examiner*—Nicky Chan
*Attorney, Agent, or Firm*—David M. Morse

[57] ABSTRACT

A new esterifying agent, i.e. methoxymethyl tosylate, is provided for use in preparing methoxymethyl esters of organic carboxylic acids. The new esterifying agent is found to be particularly advantageous in the esterification of penicillin 3-carboxyl groups or cephalosporin 4-carboxyl groups to the methoxymethyl ester group.

1 Claim, No Drawings

METHOXYMETHYL P-TOLUENESULFONATE

BACKGROUND OF THE INVENTION

1. Field of the Invention

The present invention relates to an esterifying agent and its production and use. More particularly, it relates to the esterification of organic carboxylic acids, particularly complex acids of the β-lactam type, by the use of methoxymethyl p-toluenesulfonate (methoxymethyl tosylate), a novel esterifying agent.

2. Description of the Prior Art

There is a growing need for esterification processes which can be applied to the manufacture of β-lactam antibiotics such as the penicillins and cephalosporins. It is frequently necessary to protect carboxylic acid groups in such molecules so as to enable chemical transformations to be carried out elsewhere in the molecule. Due to the known instability of the penicillins and cephalosporins, however, it is necessary to select a carboxyl-protecting group which can be both introduced and removed under sufficiently mild conditions so as not to disrupt the sensitive β-lactam ring system.

One carboxyl-protecting group which has been extensively described in the literature is the methoxymethyl ester group ($-COOCH_2OCH_3$). This ester has been found to be generally applicable as a protecting group for the 3-carboxylic acid group of a penicillin or the 4-carboxylic acid group of a cephalosporin (see, for example, U.S. Pat. Nos. 3,996,236, 3,843,639, 4,125,716 and references cited therein).

In addition to their use as intermediates for the preparation of biologically active penicillin and cephalosporin antibiotics, the methoxymethyl esters of at least certain penicillins and cephalosporins have been reported to be useful antibiotics per se, said esters being physiologically cleaved in the body to give improved blood levels and/or different tissue distribution of antibiotic compared to the corresponding unesterified compounds [see, for example, U.S. Pat. Nos. 3,996,236 (methoxymethyl ester of hetacillin) and 4,125,716 (methoxymethyl esters of hetacephalexin and hetacefadroxil)].

Preparation of methoxymethyl esters of penicillins and cephalosporins has generally been carried out with halomethyl methyl ethers such as chloromethyl methyl ether (see, for example, U.K. Pat. No. 1,488,308). Recent severe occupational restrictions on the use of chloromethyl methyl ether [Fed. Regist. 39, §1910, 93h (Jan. 29, 1974)] due to its known carcinogenicity have produced a need for a suitable substitute for the halomethyl methyl ether reagents.

Several literature references have recently appeared describing the use of dimethoxymethane (methylal) in methoxymethylation reactions, e.g. *Synthesis*, August 1977, page 567; *Synthesis*, April 1975, page 276; *Synthesis*, April 1976, page 244. From the disclosed conditions and reagents required in such processes, however, it is clear that these processes are too drastic for the relatively unstable penicillin and cephalosporin molecules.

Other literature reveals the preparation (from methylal) and use of methoxymethyl methanesulfonate (*J. Am. Chem. Soc.*, 91, 5663 (1969); U.S. Pat. No. 3,737,477). This reagent is reported to be useful as an oxyalkylating agent for ether formation. From the tremendous reactivity indicated in the *J. Am. Chem. Soc.* paper, it is clear that use of methoxymethyl methanesulfonate for introducing $-CH_2OCH_3$ on a carboxylic acid group of an unstable molecule such as a penicillin or cephalosporin was not contemplated.

It was an object of the present invention to provide a new esterifying agent for methoxymethylating the 3-carboxylic acid group of a penicillin or the 4-carboxylic acid group of a cephalosporin. Another object of the invention was to provide a method for preparing methoxymethyl esters of penicillins and cephalosporins in high yield without use of a halomethyl methyl ether reagent and without destruction of the sensitive β-lactam ring system. Still other objects and features of the invention will become apparent from the following description.

SUMMARY OF THE INVENTION

The above objectives have been met by the provision, according to the present invention, of methoxymethyl p-toluenesulfonate (methoxymethyl tosylate) having the formula

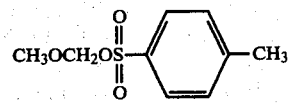

and its use as an esterifying agent for preparing methoxymethyl esters of carboxylic acids.

DETAILED DESCRIPTION

Compound I may be prepared by reaction of acetic p-toluenesulfonic anhydride with dimethoxymethane according to the equation

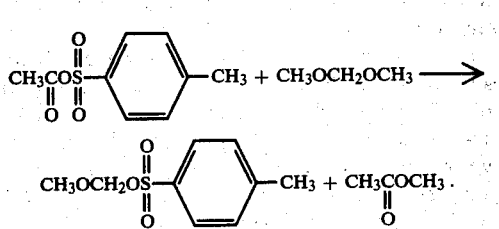

The reaction is conducted by admixing the acetic p-toluenesulfonic anhydride with an excess of the dimethoxymethane at room temperature.

Preparation of acetic p-toluenesulfonic anhydride may be accomplished by heating acetic anhydride and p-toluenesulfonic acid (preferably as the monohydrate) at 120°–130° C. according to the equation

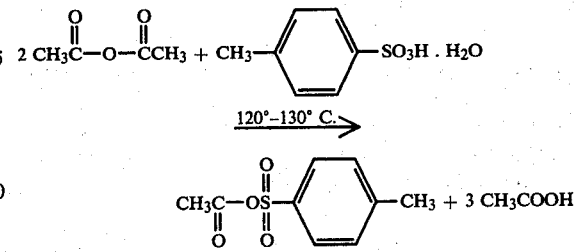

The mixed anhydride product may be obtained by removing excess acetic anhydride at about 70° C. under vacuum.

Alternatively and preferably the mixed anhydride is prepared by refluxing acetyl chloride and p-toluenesulfonic acid (preferably as the monohydrate) according to the equation

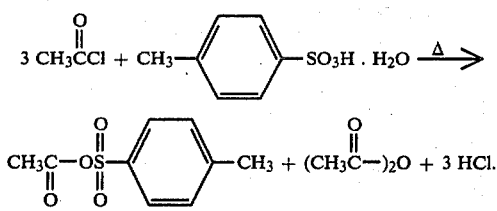

Upon removal of excess acetyl chloride, the desired product crystallizes as a snow-white solid.

The methoxymethyl tosylate of the present invention may be used to esterify the carboxyl group of an organic carboxylic acid so as to form the corresponding methoxymethyl ester. While the process is generally applicable for esterification of the carboxyl group of any organic carboxylic acid, it is particularly valuable in esterifying the 3-carboxyl group of a penicillin or the 4-carboxyl group of a cephalosporin. In the preferred process aspect of the invention, i.e. the methoxymethylation of a penicillin 3-carboxyl group or a cephalosporin 4-carboxyl group, the particular penicillin or cephalosporin used as starting material is not critical since the reaction is concerned only with esterification of the 3- or 4-carboxyl portions of the β-lactam molecules. When the starting material contains a substituent which may be influenced in the course of the esterification such as amino, hydroxyl or carboxyl, the substituent may if desired be protected prior to the methoxymethylation reaction by conventional protecting groups. Alternatively, said substituent may be left unprotected and may be allowed to react with the esterifying agent. Since the desired 3- or 4-carboxyl group is still successfully esterified, however, such side reactions do not affect the intended reaction and the overall esterification process is within the scope of the present invention.

The term "penicillin" as used herein is meant to include 6-aminopenicillanic acid (6-APA), 6-aminopenicillanic acid 1-oxide (6-APA sulfoxide) and derivatives of 6-APA or 6-APA sulfoxide having a conventional penicillin side chain in the 6-position. Thus, the penicillin starting material may have the general formula

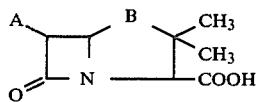

II wherein B is $=S$ or $=S-O$ and A is $NH_2$ or a conventional penicillin side chain.

The term "cephalosporin" as used herein is meant to include all known cephalosporin compounds including especially those of the general formula

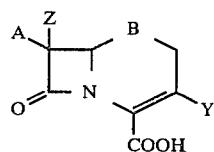

III wherein B is $=S$ or $=S-O$, A is $NH_2$ or a conventional cephalosporin side chain, Z is hydrogen or methoxy and Y is a conventional 3-substituent of a 3-cephem nucleus.

Substituent A in starting materials II and III above may be any conventional side chain previously disclosed for use as a penicillin 6-substituent or a cephalosporin 7-substituent. The nature of the A substituent is not critical for carrying out the esterification process of the present invention, but such substituent will normally be one which has been found to impart useful biological activity to a penicillin or cephalosporin nucleus. In addition to $NH_2$, A may thus be acylamino such as is present in one of the reported natural or semi-synthetic penicillins or cephalosporins. Included within acylamino are sidechains wherein an acylamino group having a free amino group, preferably an α-amino group, is reacted with an aldehyde or ketone such as formaldehyde, acetaldehyde or acetone. A preferred group of this type has the formula

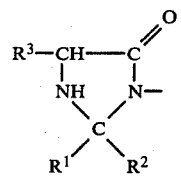

wherein either $R^1$ and $R^2$ are each methyl or $R^1$ is hydrogen and $R^2$ is methyl and wherein $R^3$ is cyclohexadienyl, 2- or 3-thienyl, phenyl or phenyl substituted by one or more, preferably one or two, of the substituents selected from halo (chloro, bromo, fluoro, iodo), hydroxy, $C_1$–$C_6$ alkyl, nitro, amino, $C_1$–$C_6$ alkanoyl, $C_1$–$C_6$ alkanoyloxy, trifluoromethyl, $C_1$–$C_6$ alkoxy, $C_1$–$C_6$ alkanoylamino or $C_1$–$C_6$ alkylthio. Most preferred members of this group are those wherein $R^3$ is phenyl or p-hydroxyphenyl and $R^1$ and $R^2$ are each methyl.

Examples of suitable A substituents are provided in U.K. Pat. No. 1,525,626 (see definition of $R^1$—NH) and in U.S. Pat. No. 4,112,230 (columns 5–16 under definition of R—NH). Illustrative of such substituents are those of the formulae:

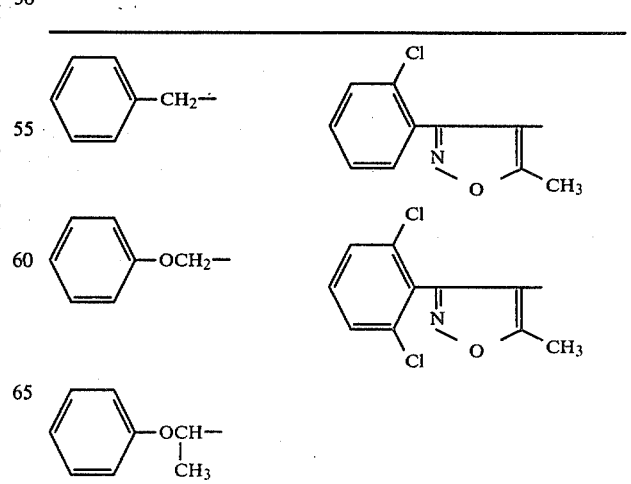

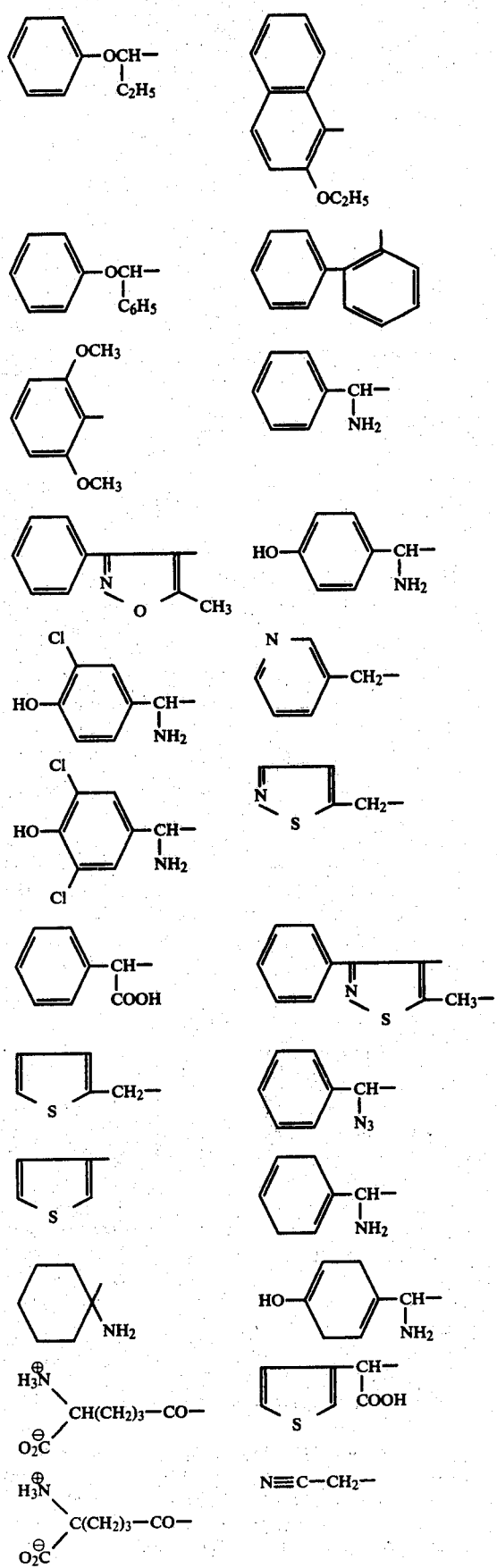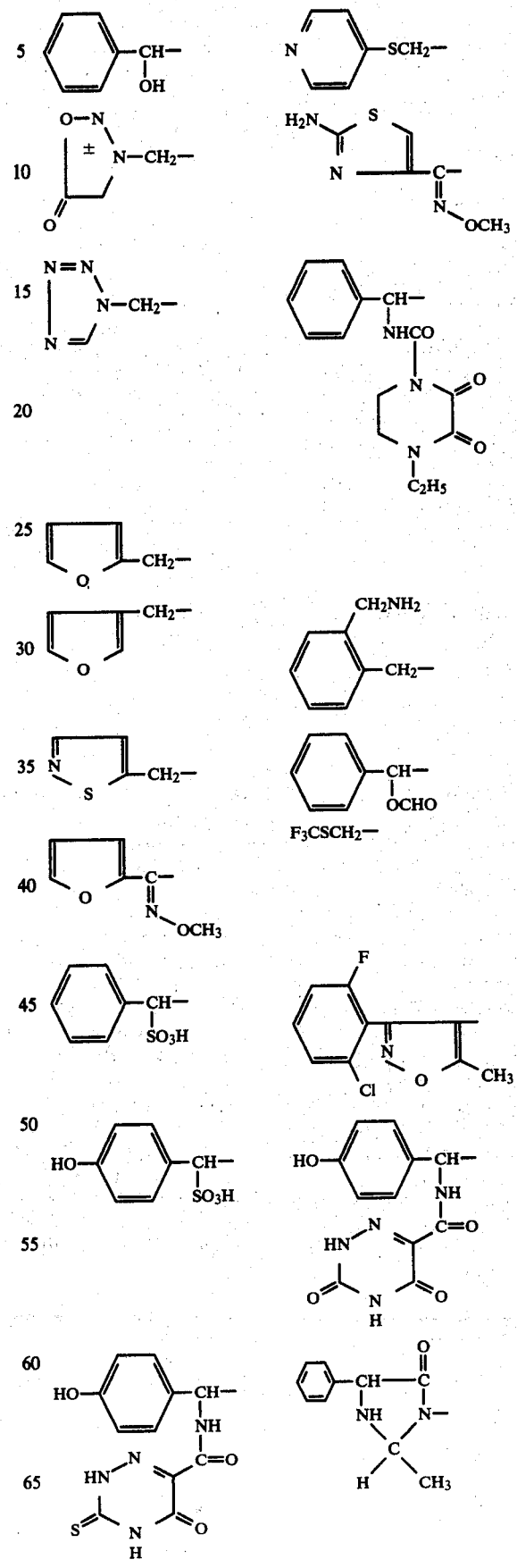

-continued

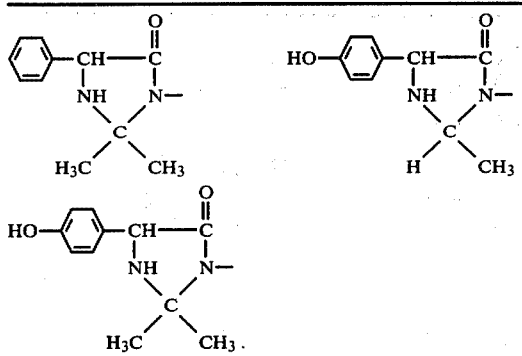

As substituent Y on the cephalosporin starting material, there may be used any conventional 3-substituent for a 3-cephem nucleus. As examples, Y may be hydrogen, halo (Cl, Br, I, F), CH$_3$, —CH$_2$OH, —CH$_2$OCOCH$_3$, —CH$_2$OCH$_3$, —CH$_2$SCH$_3$,

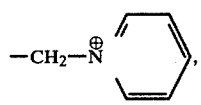

—CH$_2$OCONH$_2$, —CH$_2$SC$_6$H$_5$, —CH$_2$N$_3$,

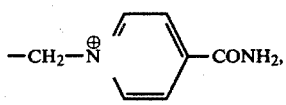

—CH$_2$OCON(CH$_3$)$_2$, —CH$_2$NH$_2$ or —SHet in which Het represents an optionally substituted 5- or 6-membered heterocyclic ring containing 1–4 atoms selected from N, O and S, the substituents on said ring being preferably one or two radicals selected from halo, C$_1$–C$_4$ alkyl, C$_1$–C$_4$ alkoxy, cyano, carboxyl, amino, nitro, trifluoromethyl, hydroxy, hydroxymethyl, C$_1$–C$_4$ alkylthio, C$_1$–C$_4$ alkylamino, di(C$_1$–C$_4$)alkylamino, mercapto, phenyl, benzyl, di(C$_1$–C$_4$)alkylamino(C$_1$–C$_4$)alkyl, —(CH$_2$)$_n$COOH and —(CH$_2$)$_n$SO$_3$H wherein n is an integer from 1 to 4. As examples of suitable heterocyclic rings there may be mentioned thienyl, furyl, pyrazolyl, imidazolyl, isoimidazolyl, triazolyl, tetrazolyl, thiazolyl, thiadiazolyl, oxazolyl, oxadiazolyl, isothiazolyl, isoxazolyl, pyridyl, pyridazinyl, pyrazinyl, pyrimidinyl and triazinyl. Especially preferred Het groups are 1,2,3-triazolyl, 2-methyl-1,3,4-thiadiazol-5-yl, 2-methyl-1,3,4-oxadiazol-5-yl, 1-N-methyltetrazolyl, 1-carboxymethyl tetrazol-5-yl and 1-carboxyethyl-tetrazol-5-yl. Typical S-Het groups would include those such as

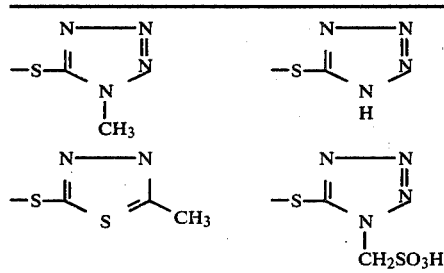

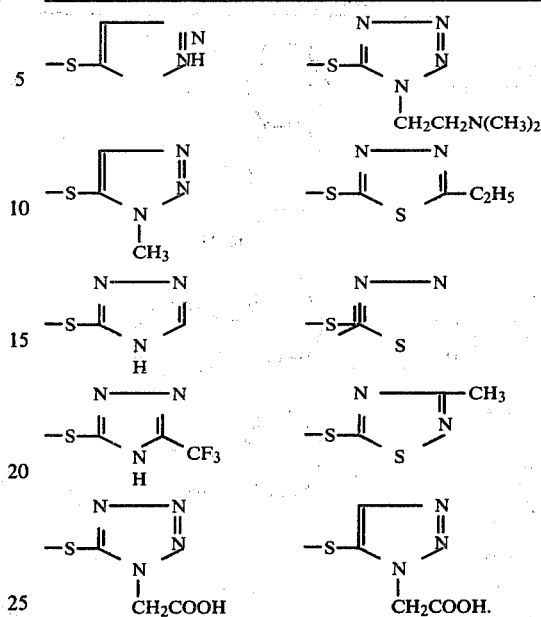

Since methoxymethyl esters are reported to be particularly useful for those penicillins and cephalosporins which are orally administered, a preferred group of starting materials for use in the present process comprises ampicillin, amoxicillin, hetacephalexin, hetacefadroxil, hetacephaloglycin, oxacillin, cloxacillin, dicloxacillin, flucloxacillin, hetacillin, metampicillin, hetaamoxicillin, cefaclor, nafcillin, meta-chlorocefadroxil, cephradine, cephalexin, cefadroxil, phenoxymethyl penicillin, phenethicillin, propicillin and phenbenicillin.

For use as intermediates, methoxymethyl esters may in general be made of any penicillin containing a 3-carboxyl group or any cephalosporin containing a 4-carboxyl group. Illustrative of such starting materials are 6-APA, 6-APA sulfoxide, 7-ACA, 7-ADCA, cephalosporin C, cephalosporin D, benzylpenicillin, methicillin, carbenicillin, cephalothin, cephaloridine, ticarcillin, cefaparole, cefatrizine, cefamandole, cefazaflur, ceforanide, cephapirin, cefoxitin, cefuroxime, cefazolin, cefotaxamine and pipericillin.

In the esterification process of the present invention, a penicillin containing a 3-carboxylic acid group or a cephalosporin containing a 4-carboxylic acid group is reacted in the form of the free acid or as a carboxylic acid salt thereof with methoxymethyl p-toluenesulfonate as the esterifying agent in a substantially anhydrous inert organic solvent and in the presence of base.

Because of the extreme sensitivity of methoxymethyl p-toluenesulfonate to water, the esterification reaction is preferably carried out in an anhydrous or substantially anhydrous inert organic solvent such as methylene chloride, acetone, methyl isobutyl ketone, acetonitrile, dimethylformamide, dimethylsulfoxide, chloroform, carbon tetrachloride, ethylene chloride or ethyl acetate. The most preferred solvent is dry methylene chloride.

The reaction proceeds most advantageously when carried out in the presence of a molar excess of an organic or inorganic base such as an alkali metal hydroxide, carbonate or bicarbonate, an alkaline earth metal hydroxide, carbonate or bicarbonate or an organic amine. Examples of suitable bases are NaOH, Ca(OH)$_2$, Mg(OH)$_2$, NaHCO$_3$, K$_2$CO$_3$, pyridine triethylamine, trimethylamine, tributylamine, diethylamine, dicyclohexylamine, N-ethylpiperidine, N-methylpiperidine, N-methylmorpholine, etc. Most preferably an organic amine base such as triethylamine is employed.

As mentioned above, the penicillin or cephalosporin starting material may be used in the form of the carboxylic acid or as a salt of the carboxylic acid such as an alkali metal, alkaline earth metal or amine salt. When the free acid is employed a salt is formed in situ upon addition of the base to the reaction mixture.

Temperatures during the esterification are not critical and may vary from about −20° C. to about +50° C. Best results, however, are generally achieved at temperatures below room temperature, preferably in the range of about −10° to +10° C.

The methoxymethyl p-toluenesulfonate is generally used in a molar excess relative to the penicillin or cephalosporin starting material. Acidic impurities (mainly p-toluenesulfonic acid) generally present at least to some degree in the methoxymethyl p-toluenesulfonate are neutralized during the reaction by the base which also serves as a solubilizing agent for the β-lactam starting materials.

Following formation of the desired methoxymethyl ester, the product is recovered by conventional procedures.

Preparation of methoxymethyl esters of penicillins or cephalosporins containing 6- or 7- side chains of the type

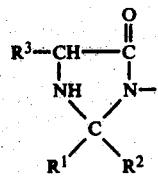

may be accomplished by reaction of the appropriate penicillin or cephalosporin acid or salt with methoxymethyl p-toluenesulfonate as described above. Alternatively, the corresponding α-amino starting material having the side chain

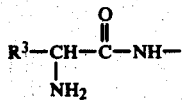

may be esterified with the methoxymethyl p-toluenesulfonate in the presence of the appropriate aldehyde or ketone (e.g. acetaldehyde or acetone) so as to form both the desired ester and sidechain in one step.

The process of the present invention has been found to give good quality product in high yields with a wide variety of penicillin and cephalosporin starting materials. Such results are quite unexpected in view of the extreme reactivity reported for the structurally similar methoxymethyl mesylate. Because of the restrictions on use of chloromethyl methyl ether, the esterifying agent previously used to form methoxymethyl esters of unstable β-lactam acids, it is believed that the present process represents a useful and commercially feasible alternative to the prior art halomethyl methyl ether process.

The following examples are given solely for purposes of illustration and not of limitation.

EXAMPLE 1

Methoxymethyl Ester of Heta-amoxicillin

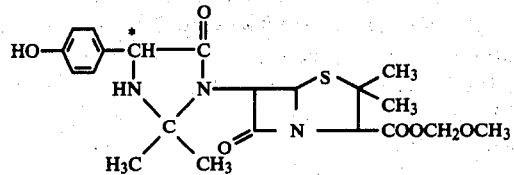

A. Preparation of Acetic p-Toluenesulfonic Anhydride

Acetyl chloride (100 ml.; density=1.104 g./ml.) was charged into a suitable reaction flask containing 30 g. (0.158 mole) p-toluenesulfonic acid monohydrate. Vigorous evolution of HCl gas occurred immediately. An efficient HCl trap was attached to the reaction system. The reaction mixture was then heated to mild reflux (∼55° C.) and was held to this temperature for 25 minutes. Heating was stopped and the reaction mixture allowed to drop to room temperature over 10–20 minutes with stirring. Vacuum (∼20–50 mm) was applied cautiously to remove acetyl chloride without carryover. At the same time the mixture was heated gradually to 60° C. Distillation of acetyl chloride was complete in ∼30 minutes with collection in an ice cold flask for reuse. The oil obtained was then subjected to vacuum (∼5–10 mm) to remove the last traces of acetyl chloride and acetic acid at 37° C. A snow white solid then crystallized in about 30 minutes as the title product.

B. Preparation of Methoxymethyl p-Toluenesulfonate

To the acetic p-toluenesulfonic anhydride obtained above was then added at room temperature 100 ml. (1.13 mole) of dimethoxymethane. The temperature of the reaction rose to 38° C. within about 5 minutes. The reaction mixture was stirred for one hour. NMR analysis indicated the title product was obtained in 90% purity after removal of excess dimethoxymethane by stripping at room temperature.

C. Preparation of Methoxymethyl Ester of Heta-amoxicillin

Heta-amoxicillin (34 g.; 0.084 mole) was suspended in 300 ml. of dry methylene chloride and 30 ml. of acetone cooled to 0°–5° C. and 22 ml. (0.158 mole) of triethylamine was then added dropwise. A complete solution was reached after about 5 minutes of stirring. To the clear solution methoxymethyl p-toluenesulfonate prepared above (dissolved in 50 ml. of dry methylene chloride) was then added dropwise over ∼10 minutes while the temperature was maintained at <5° C. The reaction mixture was stirred at 0°–5° C. for 1 hour. The reaction mixture was then poured into 200 ml. of cold (∼0° C.) water with vigorous stirring. After 5 minutes of agitation, the aqueous layer was separated (pH 7.3) and extracted once with 100 ml. of dry methylene chloride. To the combined methylene chloride solutions was added 30 ml. of acetone. The mixture was then dried with anhydrous MgSO$_4$ (14 g.) for 5 minutes at 0°–5° C. and 5 minutes without cooling. The mixture was filtered and stripped to half its volume (∼300 ml.) without heat. On addition of 50 ml. Skellysolve B (Trade name of Skelly Oil Co. for petroleum solvent comprising isomeric hexanes and having a b.p. of 60°-68° C.) or heptane to this mixture dropwise with stirring, product precipitated immediately. Another 100 ml. of Skellysolve B was added slowly with vigorous stirring. The mixture was stirred slowly for 30 minutes at room temperature and filtered to obtain a snow white solid. The filter cake was washed with 50 ml. and then 30 ml. of a 3:2 (v/v) Skellysolve B:CH$_2$Cl$_2$ mixture (cooled to $\sim$5° C.) and then with 100 ml. of Skellysolve B at room temperature. The solid was dried at $\sim$5-10 mm at room temperature for 15-20 hours. Title product was obtained (30 g.) in 80% yield. nmr quality >90%. Average bioassay=1015 mcg./mg.

D. Purification of the Methoxymethyl Heta-amoxicillin

The ester product of step C (10 g.) was dissolved in a mixture of 100 ml. CH$_2$Cl$_2$ and 100 ml. acetone. Charcoal (2 g.; Darko B) and filter aid (2 g.) were added to the mixture and it was stirred for 30 minutes at room temperature. The mixture was then filtered and the filter cake washed with 50 ml. of acetone. The volume of the filtrate was reduced in vacuum to about 30 ml. without heat. Slow addition of 9 ml. of heptane to this solution and stirring for 15 minutes resulted in heavy crystallization. The thick slurry was then cooled for 30 minutes with an ice bath, filtered and the cake washed with 10 ml. 3:2 (v/v) Skellysolve B:acetone (pre-chilled to 0° C.) followed by 10 ml. of heptane. The product was obtained in a weight yield of 49.5%. Bioassay 985 mcg./ml. Purity >95% by nmr.

EXAMPLE 2

Methoxymethyl Ester of Hetacillin

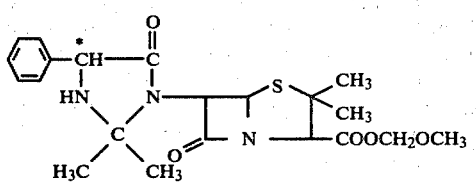

Substitution in the procedure of Example 1 of an equimolar amount of hetacillin for the heta-amoxicillin used therein gives the title product.

EXAMPLE 3

Methoxymethyl Ester of Penicillin V

Penicillin V acid (1.5 g.; 4.28 mmoles) was dissolved in 15 ml. of dry methylene chloride and 1.50 ml. of triethylamine (10.8 mmoles) were added at 0°-5° C. To this solution was added dropwise 2.2 g. of crude methoxymethyl tosylate ($\sim$79% pure) in 10 ml. of dry CH$_2$Cl$_2$. After the reaction mixture had been stirred for 1 hour at 0°-5° C., it was poured into 25 ml. of cold water. The organic phase was separated and washed with 2×25 ml. of cold water, dried with anhydrous MgSO$_4$ and stripped under vacuum to an oil which crystallized on standing. The product thus obtained, 1.48 g., 90.2% yield, had nmr and ir consistent for the structure of the title compound.

EXAMPLE 4

Methoxymethyl Ester of 7-Phenoxyacetamido-3-methyl-ceph-3-em-4-carboxylic Acid

The dicyclohexylamine salt of 7-phenoxyacetamido-3-methylceph-3-em-4-carboxylic acid (2.26 g.; 4.28 mmoles) was dissolved in 20 ml. of dry methylene chloride with 1.5 ml. (10.8 mmoles) of triethylamine at 0°-5° C. Crude methoxymethyl tosylate (2.2 g.; $\sim$79% pure, 8.04 mmoles) in 5 ml. of dry methylene chloride was added. After 45 minutes stirring at 0°-5° C., the reaction mixture was washed with 3×50 ml. of cold water. The methylene chloride layer was then dried with anhydrous MgSO$_4$ and stripped to an oil. The oil was mixed with 20 ml. of toluene followed by addition of 50 ml. of Skellysolve B. The insoluble that resulted was then dried in vacuo. Product thus obtained weighed 1.45 g. (88.6% yield) and had nmr and ir consistent for structure of the title compound.

EXAMPLE 5

Methoxymethyl Ester of Cephalosporin D Acid

Cephalosporin D (N-isobutoxycarbonyl cephalosporin C) monosodium salt (2.3 g.; 4.28 mmoles) was dissolved in 25 ml. of dry dimethylformamide with 2.4 ml. (17.2 mmoles) of triethylamine at $-5$° to $-10$° C. Crude methoxymethyl tosylate (4.4 g.; $\sim$79% purity by weight, 21% p-toluenesulfonic acid) in 10 ml. of dry methylene chloride was added dropwise. After one hour of stirring the reaction mixture was filtered to remove some precipitate and the filtrate was then poured into 100 ml. cold water and extracted with 3×50 ml. of CH$_2$Cl$_2$. The combined CH$_2$Cl$_2$ solution was then dried with anhydrous MgSO$_4$ and stripped to an oil. On trituration with diethyl ether, crystallization occurred. The product thus obtained weighed 1.1 g. (43% yield) and had nmr and ir consistent for the structure of the title compound. Workup of the ether mother liquor gave a second crop of 0.65 g. (25% yield).

EXAMPLE 6

Methoxymethyl Ester of Cefazolin

Cefazolin (1.94 g.; 4.28 mmoles) was dissolved in 20 ml. of dry methylene chloride with 1 ml. of triethylamine (7.17 mmoles) at $-5$° to $-10$° C. To this solution there was added dropwise methoxymethyl tosylate (1.46 g.; 79% purity by weight, 21% p-toluenesulfonic acid; equivalent to 5.3 mmoles pure CH$_3$OCH$_2$—OTs) in 5 ml. of dry CH$_2$Cl$_2$. The reaction mixture was stirred for 30 minutes at $-5$° to $-10$° C. and washed with 3×50 ml. cold water. The CH$_2$Cl$_2$ solution was dried and stripped to dryness. The solid thus obtained weighed 1.1 g. (51.6% yield) and had nmr and ir consistent for the structure of the title compound.

EXAMPLE 7

Methoxymethyl Ester of Penicillin V Sulfoxide

Penicillin V sulfoxide monohydrate (36.7 g., 0.095 moles) was dissolved in 200 ml. of dry CH$_2$Cl$_2$ with 21.94 ml. of triethylamine (0.1574 moles) at 0° C. Molecular sieves (type 4A; 30 g.) were added to the mixture and stirred for 30 minutes before addition of methoxymethyl tosylate (0.125 moles) in 30 ml. of dry CH$_2$Cl$_2$. The reaction mixture was stirred for another hour at 0° C. The molecular sieves were then removed by filtration and the solution poured into 300 ml. of cold water. The CH₂Cl₂ layer was separated and washed with 100 ml. of water. The CH₂Cl₂ solution was then dried and stripped under vacuum to dryness to obtain mostly crystalline solid weighed 36.3 g. (93% yield). The entire amount of solid was dissolved in 100 ml. of CH₂Cl₂, polish filtered and concentrated to 50 ml. Heptane (100 ml.) was then added with vigorous stirring and seed crystals were added. After 30 minutes of stirring a satisfactory crystal slurry had formed and another 100 ml. of heptane was slowly added. The slurry was then cooled at 0° C. for 1 hour. The crystals were filtered with suction, washed with cold heptane and dried under vacuum at room temperature for ~16 hours. There was obtained 32.0 g. of white crystals corresponding to 88% recovery. The product had ir and nmr spectra consistent for the structure of the title compound and was identical with material made earlier by the halomethyl methyl ether process.

EXAMPLE 8

If the general procedure of Examples 1–7 is repeated with the penicillin or cephalosporin used therein replaced with an equivalent amount of one of the penicillins or cephalosporins listed below, there is produced the corresponding methoxymethyl ester product.

6-aminopenicillanic acid
6-aminopenicillanic acid sulfoxide
ampicillin
amoxicillin
hetacephalexin
hetacefadroxil
hetacephaloglycin
oxacillin
cloxacillin
dicloxacillin
flucloxacillin
cefadroxil
metampicillin
cefaclor
nafcillin
meta-chlorocefadroxil
cephradine
cephalexin
phenethicillin
propicillin
phenbenicillin
7-aminocephalosporanic acid
7-aminocephalosporanic acid sulfoxide
7-aminodeacetoxycephalosporanic acid
cephalosporin C
benzylpenicillin
methicillin
carbenicillin
cephalothin
cephaloridine
ticarcillin
cefaparole
cefatrizine
cefamandole
cefazaflur
ceforanide
cephapirin
cefoxitin
cefuroxime
cefotaxamine
pipericillin
7-methoxycephalosporin C
7-(2,2,-dimethyl-5-oxo-4-[2'-thienyl]-1-imidazolidinyl)cephalosporanic acid
cephalosporin C₄.

We claim:
1. Methoxymethyl p-toluenesulfonate.

* * * * *

UNITED STATES PATENT AND TRADEMARK OFFICE
CERTIFICATE OF CORRECTION

PATENT NO. : 4,219,495

DATED : August 26, 1980

INVENTOR(S) : Jeng S. Lin and Paul D. Sleezer

It is certified that error appears in the above—identified patent and that said Letters Patent is hereby corrected as shown below:

In the Specification, Column 8, Lines 3-6, the left-hand formula should appear as follows:

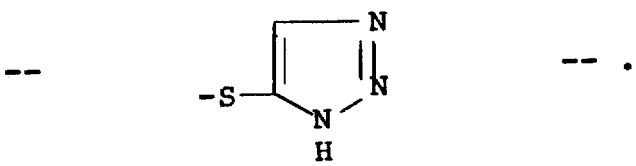

In the Specification, Column 8, Lines 13-16, the right-hand formula should appear as follows:

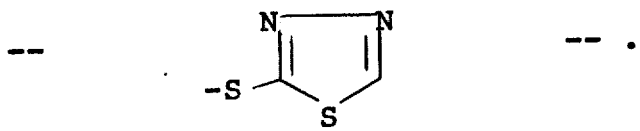

Signed and Sealed this

Twenty-eighth Day of October 1980

[SEAL]

Attest:

SIDNEY A. DIAMOND

Attesting Officer

Commissioner of Patents and Trademarks